United States Patent [19]

Prais

[11] 4,159,713
[45] Jul. 3, 1979

[54] BLOOD GAS SYRINGE

[75] Inventor: Alois G. Prais, Garfield, N.J.

[73] Assignee: Becton, Dickinson and Company, Rutherford, N.J.

[21] Appl. No.: 802,786

[22] Filed: Jun. 2, 1977

[51] Int. Cl.² ............................................. A61B 5/00
[52] U.S. Cl. .................................. 128/765; 128/218 P
[58] Field of Search ............... 128/218 P, 218 R, 234, 128/2 F

[56] References Cited

U.S. PATENT DOCUMENTS

| | | | |
|---|---|---|---|
| 1,948,982 | 2/1934 | Cutter | 128/218 P |
| 2,832,340 | 4/1958 | Dann et al. | 128/218 P |
| 3,147,753 | 9/1964 | Nogier et al. | 128/218 P |
| 3,742,949 | 7/1973 | Hill | 128/218 P |
| 4,030,498 | 6/1977 | Tompkins | 128/218 P |

Primary Examiner—John D. Yasko
Attorney, Agent, or Firm—Kane, Dalsimer, Kane, Sullivan and Kurucz

[57] ABSTRACT

The disclosure is of an improved blood gas syringe, particularly a self-filling arterial blood gas syringe. In one embodiment, the improved syringe comprises a conventional syringe barrel, a plunger rod and an elastomeric piston at the bottom of the plunger rod. The plunger rod is connected to the piston by a flexible coupling permitting the plunger rod to flex out of alignment with the piston component of the plunger without axially displacing the piston, thereby assuring that a seal is maintained between piston and syringe barrel. The syringe has several advantages over prior art blood gas syringes, such as the obviation of inadvertently drawing air into the syringe when the plunger is not kept in axial alignment therewith when being drawn back.

5 Claims, 8 Drawing Figures

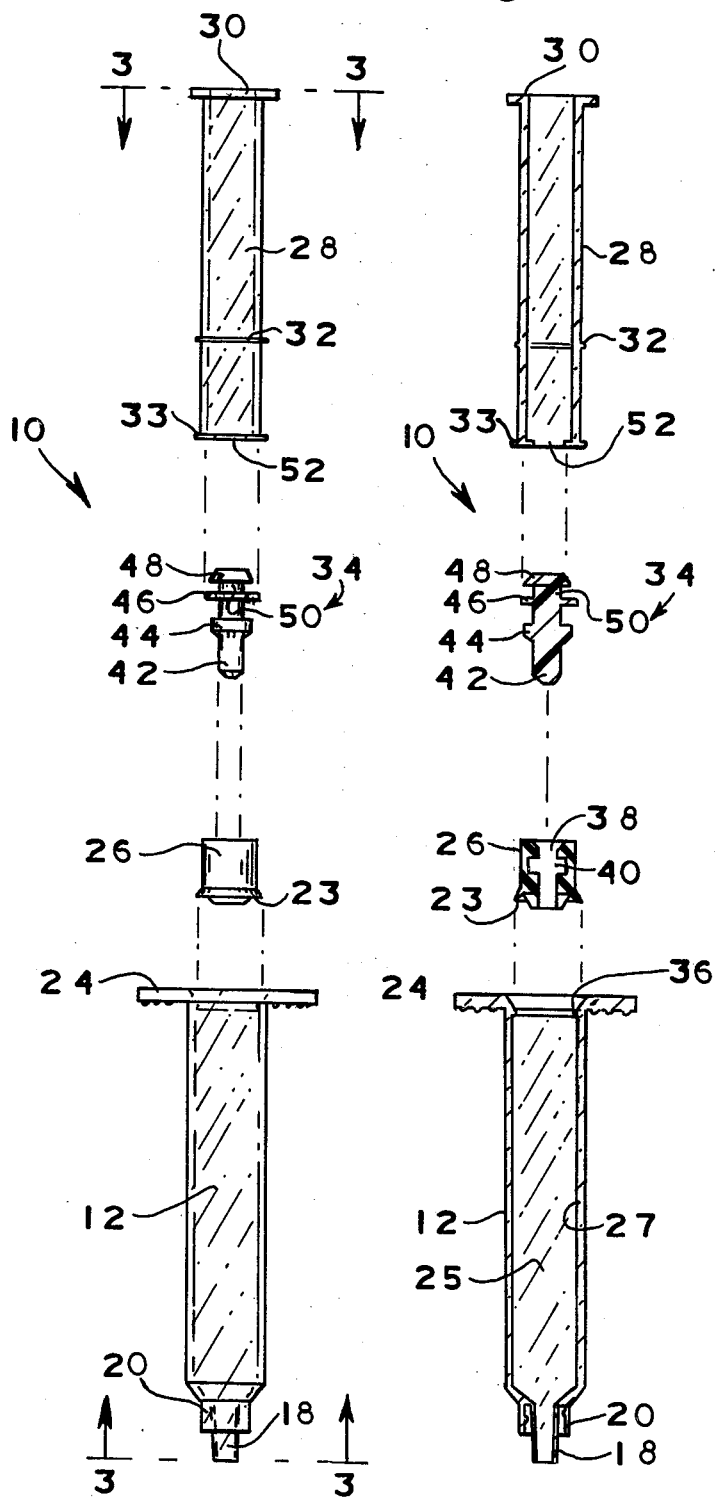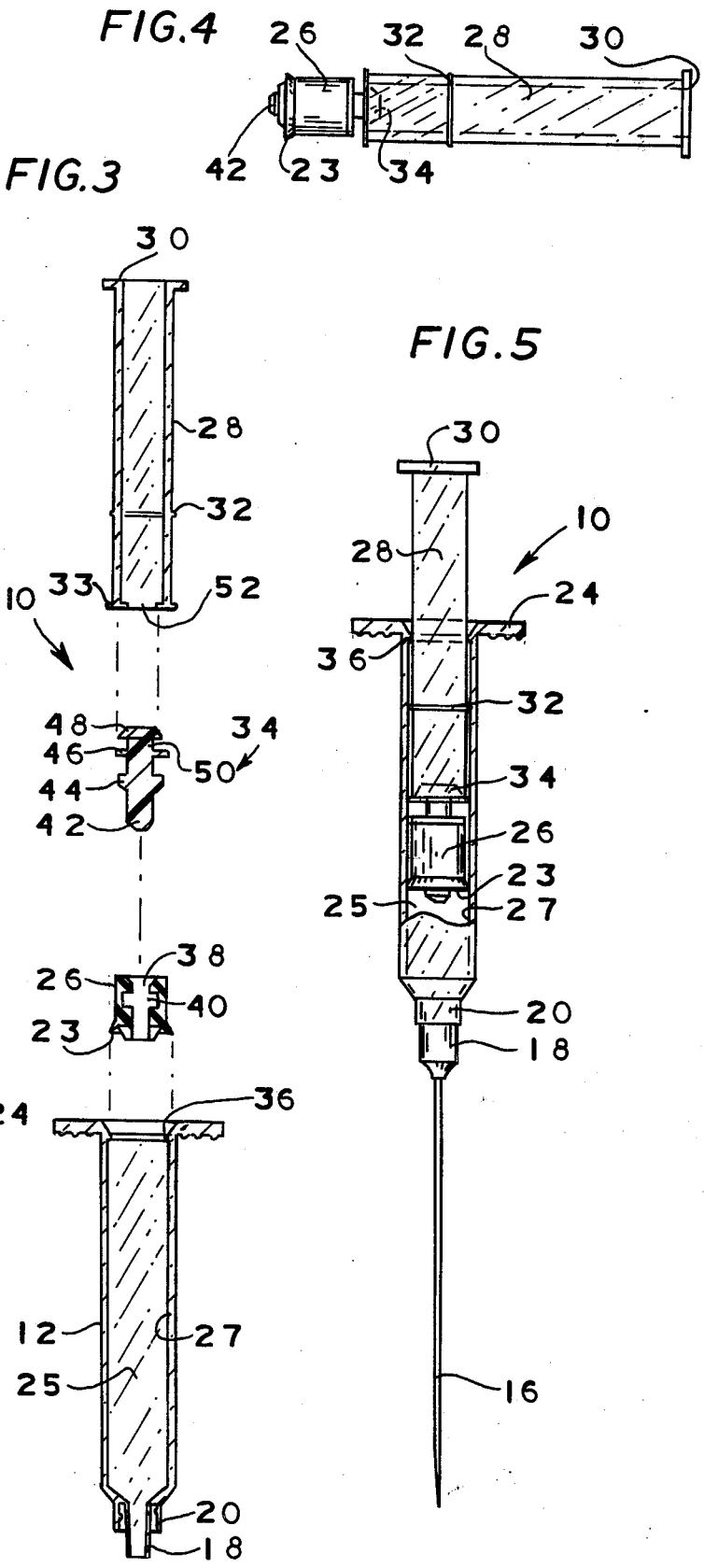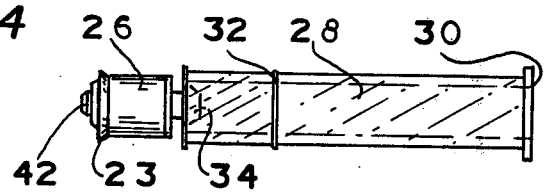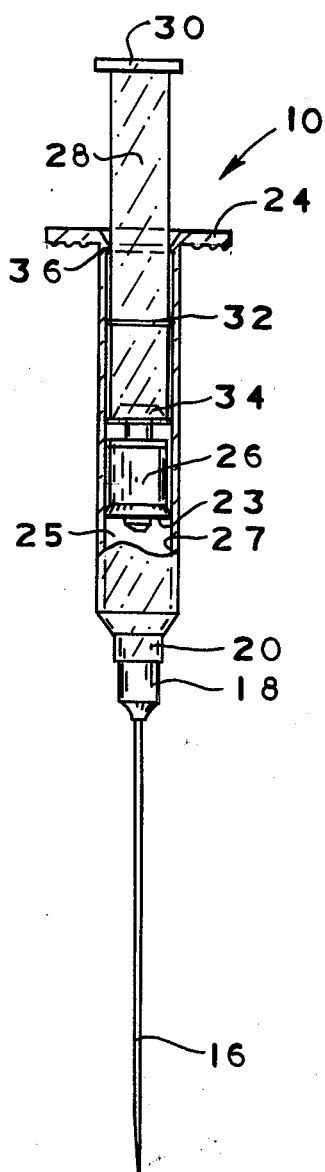

BLOOD GAS SYRINGE

BACKGROUND OF THE INVENTION

1. Field of the Invention

The invention relates to syringes and more particularly to an improved blood gas syringe.

2. Brief Description of the Prior Art

The prior art is replete with descriptions of syringes and their construction; see for example U.S. Pat. Nos. 2,869,543; 3,076,456; and 3,570,486. In spite of the highly developed state of the art a number of problems have heretofore been associated with the available syringes, particularly arterial blood gas syringes. For example, blood gas syringes of the type having minimal sealing contact between the piston component and the barrel component inadvertently leak air into the barrel if the piston is displaced from its axial alignment in the barrel. This can occur if the usually attached plunger rod is displaced axially during withdrawal of the plunger. The improved syringe of the present invention permits the piston to float freely, fairly independent of the plunger rod and to maintain its axial alignment even if the plunger rod is displaced axially. This allows for advancement or withdrawal of the piston along the barrel length in conventional manner but eliminates the possibility of specimen leakage or air contamination when the blood filled syringe is handled and transported to a laboratory for analysis.

SUMMARY OF THE INVENTION

The invention comprises a syringe, which comprises;
a cylindrical barrel having a first open end for receiving a slidable plunger, a second open end adapted to mount a needle on the opening thereof and a bore communicating between said ends; and
a plunger slidably mounted in the bore of said barrel, said plunger being at least partially withdrawable from said barrel through said first open end, said plunger comprising;
(a) an elastomeric piston having an upper end and a lower end, a body joining said upper and lower ends, said body having a diameter less than the diameter of said bore and a sealing flange radially disposed about the outer periphery of said body between the upper and lower ends, said flange forming a light sliding seal with the inner walls of said barrel;
(b) a plunger rod having a first end extending out of the first open end of said barrel and a second end within the bore of said barrel; and
(c) means for coupling said second end of said rod to the lower end of said piston, said means permitting the displacement of the first end of said rod out of axial alignment with said piston, without moving said piston out of said alignment.

The term "light sliding seal" as used herein means a sliding seal with low frictional resistance between the piston and the barrel components. Generally the resistance offered is in the order of from about 31 to about 77 grams of pull.

BRIEF DESCRIPTION OF THE DRAWINGS

FIG. 2 is an isometric view of the embodiment syringe seen in FIG. 1, but disassembled.

FIG. 3 is a cross-sectional side elevation of the embodiment syringe shown in FIG. 2.

FIG. 4 is an isometric view of the plunger component of the syringe embodiment shown in FIGS. 1-3.

FIG. 5 is another cross section in part side elevation of the embodiment syringe seen in FIG. 1 but with the plunger in a different position.

DETAILED DESCRIPTION OF THE PREFERRED EMBODIMENTS OF THE INVENTION

Figure 1:
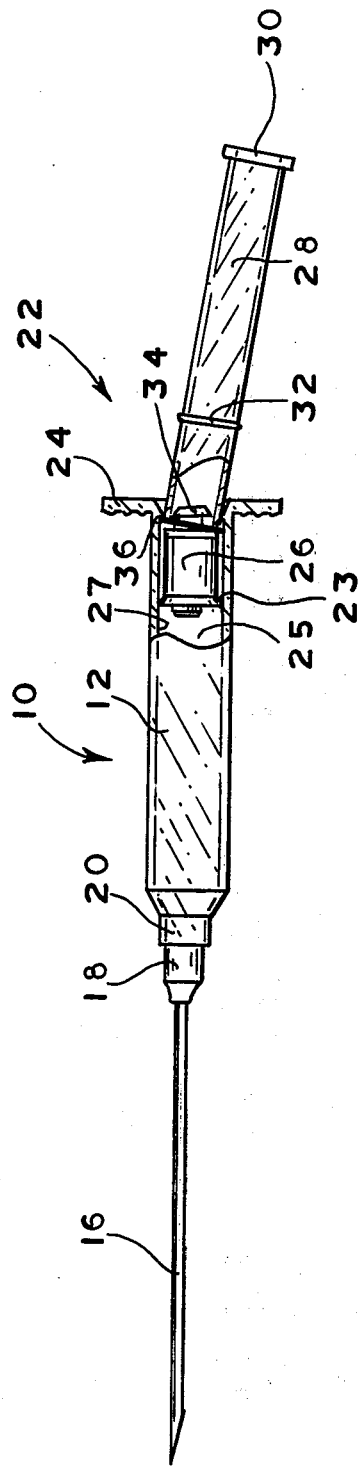
FIG. 1 is a partially cut-away side elevation of an embodiment syringe of the invention.

Representative of the syringes of the invention is the syringe 10, a cross sectional-in-part side elevation of which may be seen in FIG. 1. The syringe 10 comprises a barrel 12 having one end 20 adapted to receive and mount needle hub 18 for a hypodermic needle 16. The opposite end 22 of barrel 12 is open for receiving a slidable plunger assembly. A bore 25 traverses the interior of barrel 12, communicating between ends 20, 22. The bore 25 is defined by the inner walls 27 of barrel 12. Slidably mounted within bore 25 is the plunger assembly which comprises a piston component 26 and a plunger rod 28. Plunger rod 28 includes a handle portion 30 and in the preferred embodiment of FIG. 1 a rib 32 circumscribing the periphery of cylindrical plunger rod 28. Plunger rod 28 is connected to the piston 26 by a coupling member 34. The coupling member 34 permits the displacement of plunger rod 28 from axial alignment with the piston component 26 without affecting the alignment of the piston 26 itself. As shown in FIG. 1, the plunger assembly has been withdrawn to the end 22 of barrel 12 and in this position the plunger rod 28 has been displaced from its axial alignment with the bore 25 and the piston 26. Ordinarily, such displacement of the plunger rod 28 would cause the piston 26 to be similarly displaced from its axial alignment in bore 25, permitting misalignment and the breaking of the seal between piston 26 and the inner walls 27 of barrel 12. This would open bore 25 below piston 26 to the atmosphere through end 22. However, because of the flexibility of the coupling means between piston 26 and rod 28 displacement of the plunger rod 28 is permitted without affecting the axial alignment of piston 26 in bore 25 and the seal between piston 26, seal flange 23 and the inner walls 27 of barrel 12 remain intact.

Referring now to FIG. 2, an isometric view of the embodiment syringe 10, disassembled, further details of the syringe 10 may be seen. The syringe barrel 12 has a finger grasping flange 24 at end 22 to facilitate use of the syringe in a conventional manner. The piston 26 is shown to have a diameter less than the diameter of bore 25 so that only sealing flange 23, disposed radially about the body of the piston 26 between its upper and lower ends affects a very light seal with the inner walls 27 of barrel 12. In the most preferred embodiment syringe of the invention, flange 23 is the only contacting surface between piston 26 and barrel 12. This very light sealing arrangement between piston 26 and barrel 12 permits the use of the syringe as a self-filling, arterial blood gas syringe since there is very little friction between the piston 26 and the inner walls 27 of barrel 12. The piston 26 and its integral flange 23 are preferably made of an elastomeric, sealing material such as natural rubber, synthetic rubbers and like materials.

Referring now to FIG. 3, a cross sectional view of the syringe 10 as shown in FIG. 2, one can see that piston 26 has a bore 38 therethrough and includes a recessed portion 40 within the bore 38. Seated within the elastomeric piston 26 is a stud 34 which comprises a lead end 42 which projects from the piston 26 when inserted in bore 38. A flange 44 nests within the recess 40 of bore 38 to secure the stud 34 against movement within bore 38 of piston 26. A second flange 46 seats against the outside of piston 26 and closes the bore 38 permitting integral spacing bar 50 and stud cap 48 to project from the upper end of the piston 26. The stud cap 48 is inserted through the opening 52 in the end of plunger rod 28 and secures the plunger rod 28 to piston 26 without a rigid connection. The plunger rod 28 rides freely or "floats" on spacing bar 50 and can be rotated thereon and displaced axially from the axial center or direction of stud 34 as previously described in relation to FIG. 1. The opening 52 is of a dimension to loosely accommodate spacing bar 50 but retains the stud cap 48.

Referring now to FIG. 4, an isometric view of the plunger assembly, one can see the connection of piston 26 to plunger rod 28 through the stud 34.

Figure 6:
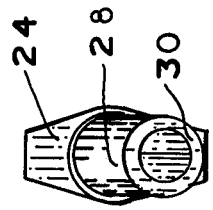
FIGS. 6-8, inclusive, are plunger end views of the embodiment syringe seen in FIG. 1 but with the plunger in various alignment positions.
Figure 7:
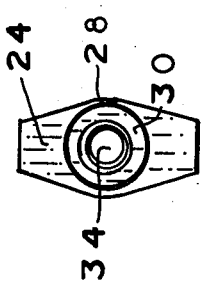
Figure 8:
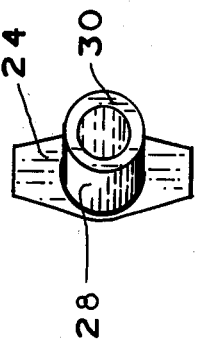

Referring now to FIG. 5, a cross section-in-part side elevation, the syringe 10 may be seen again but with the plunger rod 28 moved forward into the bore 25 of barrel 12. In a preferred embodiment assembly of syringe 10, a rib 36 circumscribes the inner walls 27 of bore 25 at end 22. The rib 36 serves as a stop means in conjunction with rib 32 circumscribing the plunger rod 28. Thus, upon withdrawal of plunger rod 28, it will be stopped by the engagement of rib 32 with rib 36. This assures that the plunger assembly is not inadvertently withdrawn from bore 25 during operation, resulting in loss of specimen. FIGS. 6, 7 and 8 are end views of the end 22 of syringe 10. One can see that the plunger rod 28 may be displaced in sidewise or up and down fashion or it may be held in axial alignment with the barrel 12 as shown in FIG. 7. With such movements, which may commonly occur after syringe 10 has been filled and is being transported to a laboratory for analysis, no leakage occurs from the end 22 of the syringe 10 because the piston 26 is maintained in its aligned position in the bore 25. Thus, there is an elimination of any possibility of specimen leakage or air contamination of the blood specimen by air leakage past sealing flange 23 when the blood filled syringe 10 is handled and transported.

Syringe 10 may be fabricated from any material conventionally used to manufacture syringes. For example, the barrel 12, plunger rod 28 and coupling 34 may be made from metal, ceramic, glass, polymeric resin such as polyethylene, polypropylene, polycarbonate and like materials.

The operation of syringe 10 is as follows. The operator gains entry into a mammalian blood vessel using conventional venipuncture technique. If entry has been made into an artery, the arterial pressure will force blood into the needle 16 and because of the light interference fit of piston 26 in barrel 12, the pressure on the face of piston 26 will force the plunger assembly towards the end 22 of barrel 12. This signals to the operator that an artery has been entered (note if the operator was seeking a vein, the lower pressure will be observed and he or she can then withdraw the needle to seek further an artery). Blood flowing into the needle bore and into hub 18 enters the barrel bore 25. Blood continues to fill bore 25 by arterial blood pressure on the lower end of piston 26, forcing the plunger assembly out of end 22 of barrel 12. Alternatively the plunger assembly may be manually withdrawn to fill bore 25. When a desired amount of blood has been obtained in the barrel 12 or the plunger rod 28 has been stopped by engagements of the ribs 32, 36 as described previously, the connection with the mammalian blood vessel is terminated in the conventional manner by withdrawal of the needle 16 from the mammal. The needle 16 may then be removed from its mounting on barrel 12 and barrel end 20 covered with a cap. The blood specimen will then have been collected without exposure of the blood to atmospheric gases in the environment and will be maintained isolated from the atmosphere. Even if in handling the plunger rod 28 is displaced axially, the seal affected by flange 23 will not be ruptured and air will not contaminate the collected blood specimen by passage past an axially displaced piston 26. The blood specimen may then be transported to a laboratory facility for gas analysis if desired.

What is claimed:

1. A blood gas syringe, which comprises;
   a barrel having a first open end for receiving a slidable plunger, a second open end adapted to mount a needle on the opening thereof and a bore communicating between said ends; and
   a plunger slidably mounted in the bore of said barrel, said plunger being at least partially withdrawable from said barrel through said first open end, said plunger comprising;
   (a) an elastomeric piston having an upper end and a lower end, a body joining said upper and lower ends, said body having a diameter less than the diameter of said bore, and a sealing flange radially disposed about the outer periphery of said body between the upper and lower ends, said flange forming a light sliding seal with the inner walls of said barrel;
   (b) a plunger rod having a first end extending out of the first open end of said barrel and a second end within the bore of said barrel; and
   (c) means for coupling without a rigid connection, said second end of said rod to the lower end of said piston, said means permitting the displacement of the first end of said rod out of axial alignment with said piston, without moving said piston out of said alignment, said means also permitting free rotation and axial movement of the rod without moving the piston, and
   wherein said means comprises a stud mounted in said piston and an opening in the second end of said rod, said stud including a spacing bar component extending distally from the connection with the piston and a stud cap at the terminal end of the spacing bar, said stud spacing bar being inserted in and retained in said opening by engagement of the stud cap with the portions of said rod defining said opening, said spacing bar being of a dimension permitting the rod to float thereon without a rigid connection between rod and piston, said rod being rotatable and axially displaceable upon the spacing bar.

2. The syringe of claim 1 having a finger grasping flange at the first open end of said barrel.

3. The syringe of claim 1 wherein said sealing flange is the only contacting surface between the piston and said barrel.

4. The syringe of claim 1 which further comprises a means for stopping the plunger assembly from complete withdrawal from the first end of said barrel.

5. The syringe of claim 4 wherein said means for stopping comprises a rib circumscribing the outer periphery of said plunger rod and a rib circumscribing the inner walls of said barrel at a point adjacent to said first open end.

* * * * *